United States Patent [19]

Hamilton et al.

[11] Patent Number: 4,708,144
[45] Date of Patent: Nov. 24, 1987

[54] AUTOMATIC SENSITIVITY CONTROL FOR A PACEMAKER

[75] Inventors: John R. Hamilton, Littleton; Robert H. Whigham, Aurora, both of Colo.

[73] Assignee: Telectronics N.V., Curacao, Netherlands Antilles

[21] Appl. No.: 915,694

[22] Filed: Oct. 6, 1986

[51] Int. Cl.$^4$ .......... A61B 5/04; H03G 3/20; A61N 1/36
[52] U.S. Cl. .......... 128/419 PG; 128/419 P; 128/419 PT; 128/696; 128/901; 128/708; 330/284
[58] Field of Search .......... 128/419 P, 695, 696, 128/901, 419 PT, 419 PG; 330/284, 144, 145

[56] References Cited

U.S. PATENT DOCUMENTS

| | | |
|---|---|---|
| 3,602,706 | 8/1971 | Levitt .......... 128/696 |
| 3,841,315 | 10/1974 | Kopp .......... 128/901 |
| 4,000,461 | 12/1976 | Barber et al. .......... 128/708 |
| 4,424,812 | 1/1984 | Lesnick .......... 128/419 PG |
| 4,438,408 | 3/1984 | Skrovanek et al. .......... 330/284 |
| 4,540,000 | 9/1985 | Doherty et al. .......... 128/696 |
| 4,560,949 | 12/1985 | Young .......... 330/284 |
| 4,563,775 | 1/1986 | Yokosuka .......... 330/284 |
| 4,592,360 | 6/1986 | Lesnick .......... 128/419 PG |

Primary Examiner—William E. Kamm
Assistant Examiner—Timothy Keegan
Attorney, Agent, or Firm—Gottlieb, Rackman & Reisman

[57] ABSTRACT

An implantable pacemaker in which the sensitivity is automatically controlled. The peak value of each R wave is measured, and a long-term average is derived. The gain of the sense channel is adjusted automatically in accordance with the average of the measured peak values.

10 Claims, 2 Drawing Figures

AUTOMATIC SENSITIVITY CONTROL FOR A PACEMAKER

DESCRIPTION

This invention relates to implantable pacemakers, and more particularly to an automatic sensitivity control therefor.

Every modern-day implantable pacemaker includes a sensing capability, whether one or both chambers are sensed. The pacemaker sensitivity is a measure of the gain of the sense amplifier. A cardiac event is sensed when the amplified input signal exceeds a threshold value. If the sensitivity is too low, i.e., the gain is too low, then some cardiac events will not be sensed because even peak signals may not exceed the threshold level. If the sensitivity is too high, on the other hand, the high gain of the amplifier may result in noise signals giving rise to erroneous sensing of cardiac events. Pacemakers provided with communications telemetry usually include a mechanism which allows the physician to set the sensitivity.

There are two disadvantages in having the physician set the sensitivity. First, adjusting the sensitivity is one more thing which the physician must remember to do, and it would be better to relieve him of this task if it is possible to do so. Second, and more important, the physician generally sees the patient only occasionally, and weeks or months may go by without the sensitivity setting being changed even though a change is in order.

It is a general object of our invention to provide an implantable pacemaker which includes an automatic sensitivity control.

In accordance with the principles of our invention, the peak signal during each pacing cycle is measured. The peak amplitudes during successive cycles are averaged over a long period of time. The time may be in the order of 24 hours but, at the very least, it is in the order of minutes. The sensitivity is adjusted in accordance with the average peak value, and it is adjusted automatically. It is adjusted in this way only on a long-term basis because changes in sensitivity are long-term phenomena.

Further objects, features and advantages of our invention will become apparent upon consideration of the following detailed description in conjunction with the drawing, in which.

Figure 1:
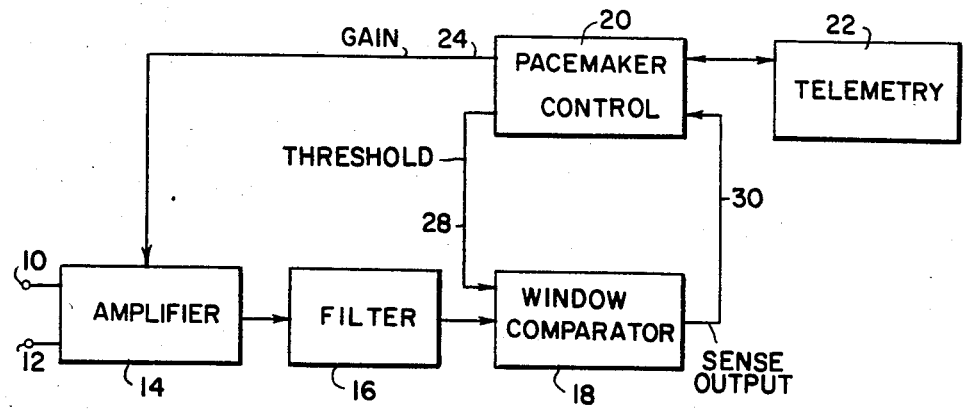
FIG. 1 depicts a prior art pacemaker without automatic sensitivity control.

The prior art pacemaker of FIG. 1 includes two input terminals 10,12 to which the electrode leads are connected. Amplifier 14 is the sense amplifier which monitors the cardiac activity. The pacemaker of FIG. 1 does not include circuitry for blanking the amplifier, circuitry for applying a pacing stimulus to the electrodes, and many other sub-systems which are well known in the art and included in a typical pacemaker. All that is shown in the drawing of FIG. 1 are those blocks which are necessary for an understanding of the present invention.

The gain of the amplifier is controlled by a signal transmitted over lead 24. The gain is determined by pacemaker control 20, which is typically a microprocessor suitably programmed.

The output of amplifier 14 is extended to bandpass filter 16. The filter typically has a center frequency of 44 Hz and a value of Q of 2. The output of the filter is extended to the input of window comparator 18.

A threshold level is applied by pacemaker control 20 over lead 28 to an input of window comparator 18. The threshold sets both limits of the window, and the window comparator checks to see whether the signal at the output of the filter falls within the two limits of the window. When the filter output is outside the window, typically when an R wave is sensed, the sense output is energized. The signal transmitted over lead 30 to pacemaker control 20 is an indication that a heartbeat has been sensed.

The system includes a telemetry section 22 which interfaces with pacemaker control 20. The physician programs the pacemaker with respect to several different parameters such as rate, pulse width and sensitivity. The sensitivity setting controls the gain of amplifier 14 and/or the threshold of window comparator 18. The term sensitivity refers to the signal at the amplifier input which is just large enough to cause the output of the comparator to go high. In the prior art, the pacemaker sensitivity has been set by the physician based upon electrocardiographic and other measurements made by him.

Figure 2:
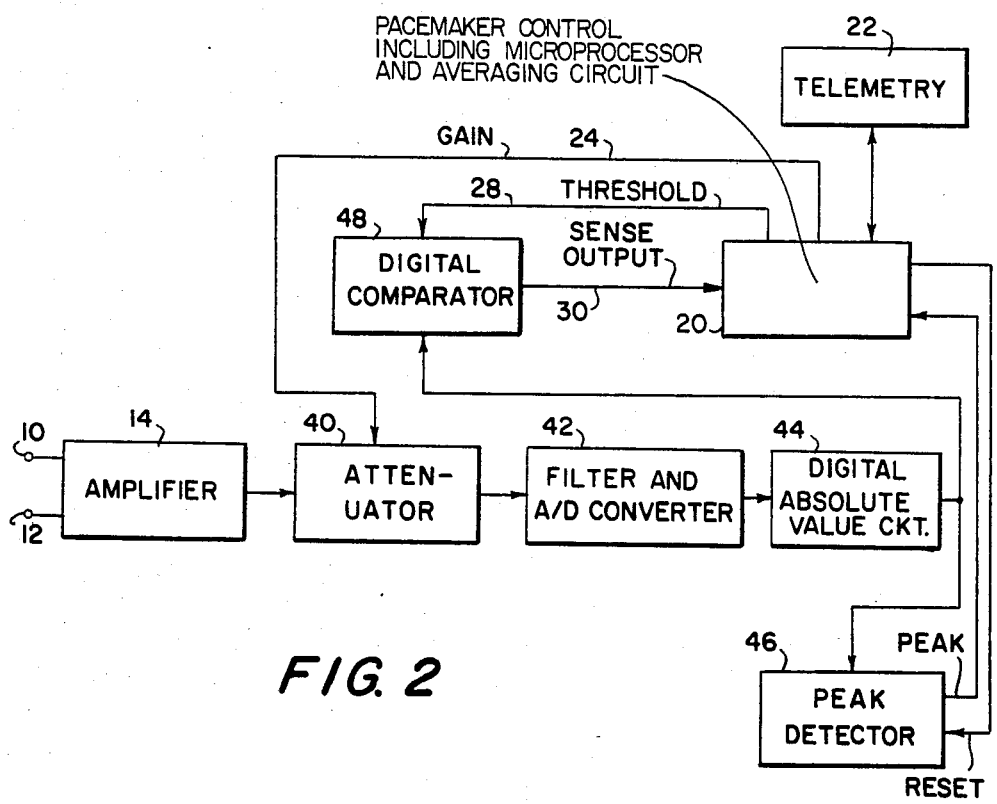
FIG. 2 depicts the illustrative embodiment of our invention.

In the pacemaker of FIG. 2, an attenuator 40 is interposed at the output of amplifier 14. The gain control lead 24 is extended to the attenuator. The amplification of the sensed signal (with an amplifier gain greater than unity) followed by a controlled attenuation is equivalent to the controlled amplification of FIG. 1.

The output of the attenuator is extended to the filter and analog-to-digital converter block 42. A circuit for performing both functions is disclosed in patent application Ser. No. 891,478 entitled "Combined Pacemaker Delta Modulator And Bandpass Filter," and filed in the name of Robert Whigham on Aug. 1, 1986. Block 42 serves as a conventional filter, and also derives a digital sample of the amplified and attenuated sensed signal once every 2 milliseconds. Preferably, the pacemaker of FIG. 2 is implemented digitally. For a description of a digital implementation, reference may be made to application Ser. No. 891,479 entitled "Pacing Pulse Compensation," and filed in the name of Robert Whigham, et al on Aug. 1, 1986.

Circuit 44 derives the digital absolute value of each sample furnished by block 42. (In case delta modulation is employed, as discussed in the above-identified Whigham applications, circuit 44 derives the absolute value of a sample of the sensed signal, not merely a delta value.) The window comparator 18 of FIG. 1 is replaced by digital comparator 48 in FIG. 2. Each sample from circuit 44 is extended to an input of digital comparator 48; the threshold value is extended over bus 28 to the other input of the comparator. The digital comparator functions in a manner comparable to that of comparator 18. The reason that the absolute value of each sample is taken is that depending on the placement of the leads, the R wave can have a higher excursion in either direction at the output of the filter. (In the case of unipolar leads, it is always the negative excursion which is the highest; however, in the case of bipolar leads, the positive excursion can be higher than the negative.) In order to reject noise to the maximum extent, the threshold should be set as high as possible. In order to set the threshold as high as possible, it is necessary to use a wave which has the highest absolute value, no matter what its polarity. It is for this reason that an absolute value circuit is employed.

In the simplest implementation of our invention, the threshold value is held at a fixed level. The sense output signal on lead 30, as in the pacemaker of FIG. 1, is an indication to the pacemaker control 20 that cardiac activity has occurred. (It is to be understood that the pacemaker of FIG. 2 also includes blanking circuitry, pulse-generating circuitry, etc., although not shown in the drawing.)

Each sample from circuit 44 is also extended to peak detector 46. Following reset of the peak detector, successive samples are delivered to its input. The largest sample of all those received subsequent to the last reset appears on the output labeled peak in the drawing. The pacemaker control 20 is thus able to determine the largest sample which was sensed subsequent to the last reset.

In the preferred embodiment of the invention, pacemaker control 20 is a microprocessor which is put to "sleep" for most of each pacing cycle, while the system waits for cardiac activity to be sensed. This is a standard technique now in the pacemaker art, and the reason for using it is that the microprocessor draws a considerable current when it is running; it is caused to "wake up" only once during each pacing cycle when cardiac activity is sensed. The other hardware can be made to draw relatively little current and, for this reason, the microprocessor implements less than all of the functions which it otherwise could. The sense output on lead 30 is in essence the wake-up signal for the microprocessor. But the fact that the input signal exceeds the threshold is not necessarily an indication that the last sample will be the largest during the current cycle. For this reason, the microprocessor has a built-in delay of 30 milliseconds after the sense output on lead 30 goes high. Only after 30 milliseconds have elapsed is the reset signal generated to reset the peak detector. By this time, the peak sample will certainly have been determined since the peak of an R wave, for example, will invariably occur within 30 milliseconds of the R wave exceeding the threshold level used to sense it. Just prior to resetting the peak detector, the pacemaker control reads the peak value.

The pacemaker control 20 adjusts the gain in accordance with the average value of the peaks detected during successive cycles. The up-dating of the average value of the peak (AP) is in accordance with the following equation:

(New $AP$) = ($X$)(old $AP$) + (1 − $X$)(new sample), where X is a value between 0 and 1. There are many ways known in the art for deriving a long-term average, and the particular manner in which the average is computed is not important. What is important is that the new output, which is the gain signal 24 extended to attenuator 40, be a measure of the peaks during at least the preceding several minutes. The larger the peaks, the less amplification that is required in order for the sensed signal to exceed the threshold. Thus, the larger the average value of the peaks, the greater is the attenuation and the less is the overall gain of the sense channel. It is in this way that the sensitivity of the sense channel is automatically controlled in accordance with the amplitude of the input signal. Typically, the attenuation level is set so that the peak signal amplitude is 2-3 times greater than the threshold level.

In the simplest form of our invention, the threshold level is fixed. In application Ser. No. 915,693, filed on even date herewith in the name of Robert Whigham and entitled "Pacemaker Noise Rejection System," there is disclosed a mechanism for ignoring peak amplitudes measured during cardiac cycles which contain noise exceeding a predetermined level. The effect of noise on the automatic sensitivity control is minimal because over the long term the noise does not influence the average peak value to any significant degree. Nevertheless, especially with active people, muscle noise could affect the average peak level if the average is taken over a short period of time. When the Whigham technique is incorporated in the system of FIG. 2, e.g., implemented by the microprocessor in pacemaker control 20, the peak values which occur in the presence of noise are excluded from the average. When this is done, the average can be taken over a much shorter period of time, perhaps as little as just a few (e.g., 2) minutes. It is only in the presence of noise that the average should be taken over a long period of time, e.g., in the order of hours, so that the noise has little effect on the average value. [In the equation above for computing the new average peak value, the larger the value of X, the longer the effective interval over which the average is taken.]

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:

1. An automatic sensitivity control for an implantable pacemaker comprising means for sensing a cardiac signal, means for amplifying said cardiac signal, means for comparing the amplified cardiac signal with a threshold value for determining the occurrence of a cardiac event, means for measuring the peak amplitude of said amplified cardiac signal for the determined cardiac event, means for deriving a value representative of the average of the measured peak amplitudes during a preceding time interval which is at least a few minutes long, and means for varying the gain of said amplifying means in accordance with said derived value.

2. An automatic sensitivity control for an implantable pacemaker in accordance with claim 1 wherein said value deriving means including means for sensing the presence of noise during a cardiac cycle and for excluding from the derived value any measured peak amplitude for a cardiac event which occurs during a cardiac cycle which contains noise exceeding a predetermined level.

3. An automatic sensitivity control for an implantable pacemaker in accordance with claim 1 wherein said comparing means, said measuring means and said value deriving means all operate digitally.

4. An automatic sensitivity control for an implantable pacemaker in accordance with claim 1 wherein said value deriving means includes means for delaying the derivation of said value following the determination of the occurrence of a cardiac event for a predetermined interval to ensure that the peak amplitude of such cardiac event is measured.

5. An automatic sensitivity control for an implantable pacemaker in accordance with claim 1 wherein said amplifying means includes an amplifier having a gain greater than unity and a connected attenuator whose degree of attenuation is controlled in accordance with the magnitude of said derived value.

6. An automatic sensitivity control for an implantable pacemaker in accordance with claim 1 wherein said amplifying means, said comparing means, said measuring means and said varying means are dedicated digital circuits, and said value deriving means is a microprocessor which halts its operation between cardiac events.

7. A method for improving the determination of the occurrence of a cardiac event comprising the steps of sensing a cardiac signal, amplifying said cardiac signal, comparing the amplified cardiac signal with a threshold value for determining the occurrence of a cardiac event, deriving a value representative of the average of the measured peak amplitudes during a preceding time interval which is at least a few minutes long, and varying the gain of said amplifying means in accordance with said derived value.

8. A method in accordance with claim 7 wherein in said value deriving step the presence of noise is sensed during a cardiac cycle and any measured peak amplitude for a cardiac event which occurs during a cardiac cycle which contains noise exceeding a predetermined level is excluded from the derived value.

9. A method in accordance with claim 7 wherein said comparing step, said measuring step and said value deriving step are all implemented digitally.

10. A method in accordance with claim 7 wherein the performance of said value deriving step is delayed following the determination of the occurrence of a cardiac event for a predetermined interval to ensure that the peak amplitude of such cardiac event is measured.

* * * * *